United States Patent [19]

Parker et al.

[11] Patent Number: 5,532,400
[45] Date of Patent: Jul. 2, 1996

[54] 2,6-DI-ALKYL-4-SILYL-PHENOLS AS ANTIATHEROSCELEROTIC AGENTS

[75] Inventors: Roger A. Parker, Cincinnati; Simon J. T. Mao, Loveland, both of Ohio

[73] Assignee: Merrell Pharmaceuticals Inc., Cincinnati, Ohio

[21] Appl. No.: 353,736

[22] Filed: Dec. 12, 1994

Related U.S. Application Data

[63] Continuation of Ser. No. 219,230, Mar. 29, 1994, abandoned, which is a continuation of Ser. No. 72,347, Jun. 4, 1993, abandoned, which is a continuation of Ser. No. 940,774, Sep. 1, 1992, abandoned, which is a continuation of Ser. No. 881,395, Dec. 20, 1991, abandoned, which is a division of Ser. No. 548,052, Jul. 5, 1990, Pat. No. 5,155,250.

[51] Int. Cl.$^6$ ................ C07F 7/08; C07F 7/18
[52] U.S. Cl. ........................................... 556/449
[58] Field of Search .................... 514/63; 556/449

[56] References Cited

U.S. PATENT DOCUMENTS

| | | | |
|---|---|---|---|
| 3,328,450 | 6/1967 | Plueddemann | 556/449 |
| 3,506,674 | 4/1970 | Berger. | |
| 3,586,705 | 6/1971 | Owen et al. | 556/449 |
| 3,801,617 | 4/1974 | Fletcher. | |
| 3,853,776 | 12/1974 | Clark et al.. | |
| 4,374,742 | 2/1983 | Evans et al. | 556/449 X |
| 4,636,573 | 1/1987 | Pastor et al. | 556/427 X |
| 4,663,314 | 5/1987 | Hayase et al. | 556/427 X |
| 4,783,495 | 11/1988 | Pastor et al. | 556/449 X |
| 4,804,653 | 2/1989 | Strunk et al. | 556/427 X |
| 4,879,783 | 4/1983 | Melvin et al. | 514/63 |
| 5,117,028 | 5/1992 | Knorr. | |
| 5,138,012 | 8/1992 | Riding et al. | 556/449 X |

*Primary Examiner*—Paul F. Shaver
*Attorney, Agent, or Firm*—Louis J. Wille

[57] ABSTRACT

This invention relates to certain 2,6-di-alkyl-4-silyl-phenols which are useful as inhibitors of LDL lipid peroxidation and as antiatherosclerotic agents.

7 Claims, No Drawings

2,6-DI-ALKYL-4-SILYL-PHENOLS AS ANTIATHEROSCELEROTIC AGENTS

This is a continuation, of application Ser. No. 08/219,230, filed Mar. 29, 1994, now abandoned, which is a continuation of application Ser. No. 08/072,347, filed Jun. 4, 1993, now abandoned; which is a continuation of application Ser. No. 07/940,774, filed Sep. 1, 1992, now abandoned; which is a continuation of application Ser. No. 07/881,395, filed Dec. 20, 1991, now abandoned; which is a divisional of application Ser. No. 07/548,052, filed Jul. 5, 1990, now U.S. Pat. No. 5,155,250, which is herein incorporated by reference.

BACKGROUND OF THE INVENTION

Atherosclerosis as manifested in its major clinical complication, ischaemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, *Ann. Rev. Biochem.* 52, 223 (1983); Miller, *Ann. Rev. Med.* 31, 97 (1980)]. For example, in various epidemiologic studies the LDL cholesterol levels correlate well with the risk of coronary heart disease whereas the HDL cholesterol levels are inversely associated with coronary heart disease [Patton et al., *Clin. Chem.* 29, 1890 (1983)]. It is generally accepted by those skilled in the art that reduction of abnormally high LDL cholesterol levels is effective therapy not only in the treatment of hypercholesterolemia but also in the treatment of atherosclerosis.

Furthermore, there is evidence based on animal and laboratory findings that peroxidation of LDL lipid, such as the unsaturated fatty acid portions of LDL cholesteryl esters and phospholipids, facilitates the accumulation of cholesterol in monocyte/macrophages which eventually are transformed into foam cells and become deposited in the sub-endothelial space of the vessel wall. The accumulation of foam cells in the vessel wall is recognized as an early event in the formation of an atherosclerotic plaque. Thus it is believed that peroxidation of LDL lipid is an important prerequisite to the facilitated accumulation of cholesterol in the vessel wall and the subsequent formation of an atherosclerotic plaque. For example, it has been shown that monocyte/macrophages take up and degrade native LDL at relatively low rates and without marked accumulation of cholesterol. In contrast, oxidized LDL is taken up by these monocyte/macrophages at much higher rates and with marked accumulation of cholesterol [Parthasarathy et al., *J. Clin. Invest.* 77, 641 (1986)]. It is therefore desireable to provide methods of inhibiting LDL lipid peroxidation in a patient in need thereof.

The present invention relates to certain 2,6-di-alkyl-4-silyl-phenols which are useful as inhibitors of LDL lipid peroxidation and as antiatherosclerotic agents.

SUMMARY OF THE INVENTION

The present invention provides novel compounds of the formula (1)

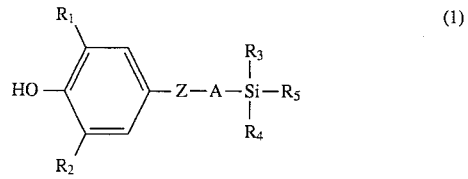

wherein $R_1$, $R_2$, $R_3$ and $R_4$ are each independently a $C_1$–$C_6$ alkyl group;

Z is a thio, oxy or methylene group;

A is a $C_1$–$C_4$ alkylene group; and $R_5$ is a $C_1$–$C_6$ alkyl or —$(CH_2)_n$—(Ar) wherein n is an integer 0, 1, 2 or 3; and Ar is phenyl or napthyl unsubstituted or substituted with one to three substituents selected from the group consisting of hydroxy, methoxy, ethoxy, chloro, fluoro or $C_1$–$C_6$ alkyl.

The present invention provides a method of inhibiting the peroxidation of LDL lipid in a patient in need thereof comprising administering to said patient an effective antioxidant amount of a compound of formula (1).

The present invention further provides a method of inhibiting the progression of atherosclerosis in a patient in need thereof comprising administering to said patient an effective antiatherosclerotic amount of a compound of formula (1).

DETAILED DESCRIPTION OF THE INVENTION

As used herein, the term "$C_1$–$C_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

Likewise, the term "$C_1$–$C_4$ alkylene" refers to a saturated hydrocarbyldiyl radical of straight or branched configuration made up of from one to four carbon atoms. Included within the scope of this term are methylene, 1,2-ethane-diyl, 1,1-ethane-diyl, 1,3-propane-diyl, 1,2-propan-ediyl, 1,3-butane-diyl, 1,4-butane-diyl and the like.

In those instances wherein $R_5$ is a —$(CH_2)_n$—(Ar) radical, the "—$(CH_2)_n$—" moiety represents a saturated hydrocarbyldiyl radical of straight chain configuration. The term "n" is defined as an integer 0, 1, 2 or 3. The moiety "—$(CH_2)_n$—" thus represents a bond, methylene, 1,2-ethanediyl or 1,3-propanediyl. The "—(Ar)" moiety represents an aryl radical defined as a substituted or unsubstituted phenyl or napthyl group. In those instances wherein the —(Ar) moiety is a substituted aryl, the phenyl or napthyl can bear from 1 to 3 substituents in any position otherwise occupied by a hydrogen atom. Substituents are selected from the group consisting of hydroxy, methoxy, ethoxy, chloro, fluoro and $C_1$–$C_6$ alkyl. Specifically included within the scope of the term "—$(CH_2)_n$—(Ar)" are phenyl; napthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The compounds of formula (1) can be prepared by utilizing procedures and techniques well known and appreciated by one of ordinary skill in the art. A general synthetic scheme for preparing compounds of formula (1) wherein Z is sulfur or oxygen is set forth in Scheme A, wherein all substituents, unless otherwise indicated, are previously defined.

Scheme A

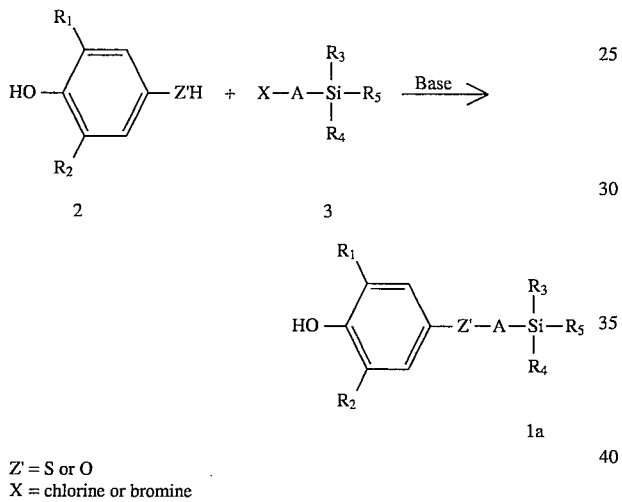

Z' = S or O
X = chlorine or bromine

In general, a phenol of structure 1a can be prepared by reacting the appropriate 2,6-dialkyl-4-mercaptophenol or 2,6-dialkylhydroquinone of structure 2 (or suitably protected derivatives) with a non-nucleophilic base, such as sodium hydride or potassium carbonate, and the appropriate haloalkylenesilane of structure 3, such as the appropriate chloroalkylenesilane, in a suitable aprotic solvent, such as dimethylformamide or dimethylacetamide.

Starting materials for use in the general synthetic procedure outlined in Scheme A are readily available to one of ordinary skill in the art. For example, certain phenol starting materials for various compounds of formula (1) wherein Z is sulfur, such as 2,6-di-tertiarybutyl-4-mercaptophenol, are described in U.S. Pat. No. 3,576,883, U.S. Pat. No. 3,952,064, U.S. Pat. No. 3,479,407 and in Japanese Patent Application 73-28425. Also, silyl starting materials for various compounds of formula (1), such as (trimethylsilyl)methyl iodide, (trimethylsilyl)methyl bromide, (trimethylsilyl)methyl chloride, (1-chloropropyl)trimethylsilane, are described in *Synthesis* 4, 318–19 (1988) and *J. Am. Chem. Soc.* 105, 5665–75 (1983).

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydropyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

In those instances where $R_1$ and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "mp" refers to melting point; "mg" refers to milligrams; "µM" refers to micromolar; "µg" refers to micrograms.

EXAMPLE 1

2,6-Di-t-butyl-4[(dimethylphenylsilyl)methyl]thio-phenol

Mix 2,6-di-t-butyl-4-mercaptophenol (2.4 g, 10 mmol), potassium carbonate (1.4 g, 10 mmol), chloromethyldimethylphenylsilane (1.9 g, 10 mmol) and dimethylformamide (50 mL) and stir overnight at room temperature under argon atmosphere. Dilute the mixture with ice-water and extract with ethyl ether. Wash the ethereal layer with water, then brine, filter through flourosil-$Na_2SO_4$, and evaporate to an orange oil (3.5 g). Purify the product by first distilling (bp 160°–170° C. @ 0.1 mm Hg), then subjecting to silica gel chromatography ($CCl_4$:$CHCl_3$/1:1) to obtain the title compound as a light yellow oil which slowly crystallizes to a white waxy solid (2.3 g, 59%).
Anal. Calcd for $C_{23}H_{34}OSSi$: C, 71.44; H, 8.86; S, 8.29; Found: C, 71.14; H, 8.86; S, 7.98.

EXAMPLE 2

2,6-Di-t-butyl-4[(dimethyldodecylsilyl)methyl]thio-phenol

Mix 2,6-di-t-butyl-4-mercaptophenol (2.4 g, 10 mmol), potassium carbonate (1.7 g, 12.3 mmol), chloromethyldodecyldimethylsilane (2.8 g, 10 mmole) and dimethylformamide (50 mL) and stir overnight at room temperature under argon atmosphere. Dilute the mixture with ice-water, acidify with aqueous hydrochloric acid and extract with ethyl ether. Wash the ethereal layer with water, then brine, filter through fluorosil-$Na_2SO_4$ and evaporate to an orange semi-solid (4.0 g). Purify the product by first distilling (180°–200° C. @ 0.1 mm Hg) then subjecting to silica gel chromatography ($CCl_4$) to obtain the title compound as a colorless oil which slowly crystallizes.
Anal. Calcd for $C_{29}H_{54}OSSi$: C, 72.73; H, 11.37; S, 6.70; Found: C, 71.26; H, 11.34; S, 6.93.

EXAMPLE 3

2,6-Di-t-butyl-4[(trimethylsilyl)methyl]thio-phenol

Mix 2,6-di-t-butyl-4-mercaptophenol (2.4 g, 10 mmol), potassium carbonate (1.4 g, 10 mmol), and dimethylacetamide (50 mL) and stir at room temperature under argon atmosphere. Add chloromethyltrimethylsilane (1.3 g, 10 mmol) and stir overnight. Warm on a steam bath for 2 hours, cool, and dilute with water. Extract with ethyl ether, dry, evaporate to a light yellow solid (2.8 g) and recrystallize (CH$_3$CN) to give 1.1 g (34%) of the title compound; mp 100°–101° C.

Anal. Calcd for C$_{18}$H$_{32}$OSSi: C, 66.60; H, 9.88; S, 9.88; Found: C, 66.83; H, 10.05; S. 9.91.

EXAMPLE 4

2,6-Dimethyl-4[(trimethylsilyl)methoxy]phenol

Mix 2,6-dimethylhydroquinone (1.4 g, 10 mmol), potassium carbonate (1.4 g, 10 mmol), chloromethyltrimethylsilane (1.9 g, 10 mmol) and dimethylformamide (50 mL). Stir at room temperature under inert atmosphere until the reaction is complete. Dilute the mixture with ice-water and extract with ethyl ether. Wash the ethereal layer with water, then brine and filter through fluorosil-Na$_2$SO$_4$. Evaporate to give the title compound and purify by silica gel chromatography.

The following compounds can be prepared by procedures analogous to those described above in Examples 1–4:
2,6-di-t-butyl-4[(triethylsilyl)methyl]thiophenol
2,6-di-t-butyl-4[(diethylphenylsilyl)methyl]thiophenol
2,6-di-t-butyl-4[(tripropylsilyl)methyl]thiophenol
2,6-di-t-butyl-4[(dipropylphenylsilyl)methyl]thiophenol
2,6-di-t-butyl-4[(triisopropylsilyl)methyl]thiophenol
2,6-di-t-butyl-4[(diisopropylphenylsilyl)methyl]thiophenol
2,6-di-t-butyl-4[(tributylsilyl)methyl]thiophenol
2,6-di-t-butyl-4[(dibutylphenylsilyl)methyl]thiophenol
2,6-di-t-butyl-4[(triisobutylsilyl)methyl]thiophenol
2,6-di-t-butyl-4[(diisobutylphenylsilyl)methyl]thiophenol
2,6-di-t-butyl-4[(tri-t-butylsilyl)methyl]thiophenol
2,6-di-t-butyl-4[(di-t-butylphenylsilyl)methyl]thiophenol
2,6-di-methyl-4[(trimethylsilyl)methyl]thiophenol
2,6-di-methyl-4[(dimethylphenylsilyl)methyl]thiophenol
2,6-di-methyl-4[(dibutylphenylsilyl)methyl]thiophenol
2,6-di-methyl-4[(tri-t-butylsilyl)methyl]thiophenol
2,6-di-methyl-4[(di-t-butylphenylsilyl)methyl]thiophenol
2,6-di-ethyl-4[(trimethylsilyl)methyl]thiophenol
2,6-di-ethyl-4[(dimethylphenylsilyl)methyl]thiophenol
2,6-di-ethyl-4[(tri-t-butylsilyl)methyl]thiophenol
2,6-di-ethyl-4[(di-t-butylphenylsilyl)methyl]thiophenol
2,6-di-propyl-4[(trimethylsilyl)methyl]thiophenol
2,6-di-propyl-4[(dimethylphenylsilyl)methyl]thiophenol
2,6-di-isopropyl-4[(trimethylsilyl)methyl]thiophenol
2,6-di-isopropyl-4[(dimethylphenylsilyl)methyl]thiophenol
2,6-di-butyl-4[(trimethylsilyl)methyl]thiophenol
2,6-di-butyl-4[(dimethylphenylsilyl)methyl]thiophenol
2,6-dimethyl-4[(trimethylsilyl)methoxy]phenol
2,6-dimethyl-4[(dimethylphenylsilyl)methoxy]phenol
2,6-dibutyl-4[(triethylsilyl)methoxy]phenol
2,6-dibutyl-4[(diethylsilyl)methoxy]phenol
2,6-di-t-butyl-4[(trimethylsilyl)methoxy]phenol
2,6-di-t-butyl-4[(dimethylphenylsilyl)methoxy]phenol.

A general synthetic scheme for preparing compounds of formula 1 wherein Z is methylene is set forth in Scheme B, wherein all substituents, unless otherwise indicated, are previously defined.

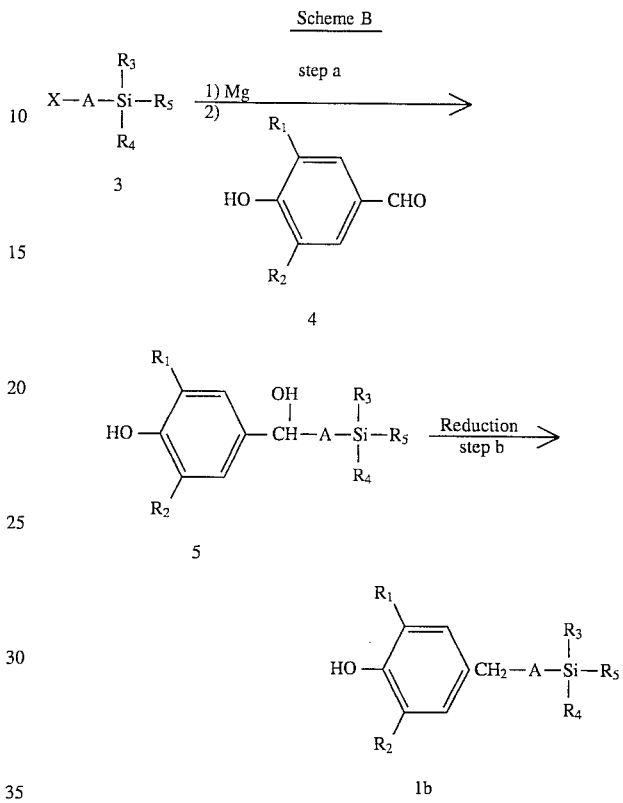

Scheme B

In general, a phenol of structure 1b can be prepared according to Scheme B in a two-step process. In step a, the appropriate haloalkylenesilane of structure 3 is reacted with magnesium metal in a suitable aprotic solvent, such as ethyl ether, in order to form the magnesium halide salt. The magnesium halide salt (Grignard reagent) is then reacted with the appropriate 3,5-dialkyl-4-hydroxy-benzaldehyde of structure 4 (or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

Starting materials for use in the general synthetic procedures outlined in Scheme B are readily available or can readily be prepared according to standard techniques and procedures. Where necessary to prevent undesired side reactions, the 1-phenol functionality of the 3,5-dialkyl-4-hydroxy-benzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

EXAMPLE 5

2,6-Dimethyl-4[2-(trimethylsilyl)ethyl]phenol

Step a: Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 3,5-dimethyl-4-hydroxybenzaldehyde (1.5 g, 10 mmol) in anhydrous ethyl ether. Stir until reaction is complete. Cool the reaction mixture to 0° C. and add saturated ammonium chloride solution. Separate the ether layer, wash with water and dry (MgSO4). Evaporate to give 4-hydroxy-3,5-dimethyl-α-[(trimethylsilyl)-methyl]benzenemethanol and purify by silica gel chromatography.

Step b: Mix sodium metal (520 mg, 22.6 mmol) and liquid ammonia (13 mL). To this solution add, by dropwise addition, a solution of 4-hydroxy-3,5-dimethyl-α-[(trimethylsilyl)-methyl]benzenemethanol (2.22 g, 10 mmol) in ethyl alcohol (0.5 g) and ethyl ether (5ml). After the blue color disappears, cautiously add water (13 mL), extract with ethyl ether, dry (MgSO$_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

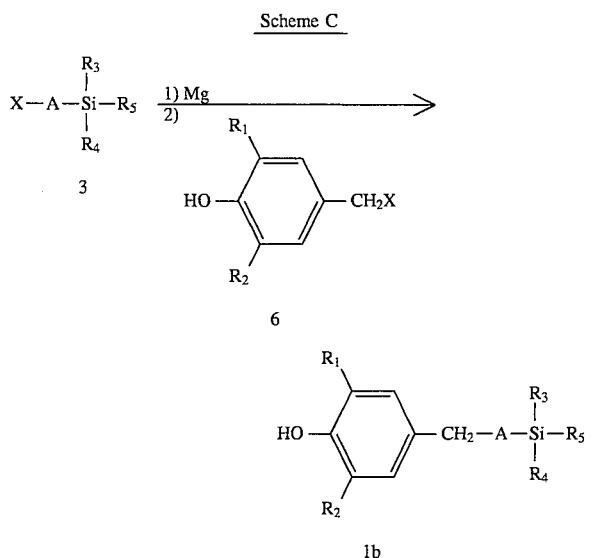

In general, a pehnol of the structure 1b can be prepared by first reacting the appropriate haloalkylenesilane of structure 3 with magnesium metal in an suitable aprotic solvent, such as ethyl ether, in order to form the magnesium halide salt. The magnesium halide salt (Grignard Reagent) is then reacted with the appropriate 3,5-dialkyl-4-hydroxy-benzylhalide of structure 6 (or a suitably protected derivative) to give the desired phenol of structure 1b.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxy-benzylbromide can be converted to the corresponding phenolic starting material by standard hydrolytic procedures.

Where necessary to prevent undesired side reactions, the 1-phenol functionality of the 3,5-dialkyl-4-hydroxy-benzylhalide of structure 6 in Scheme C may be blocked prior to the Grignard reaction with a standard phenol blocking agent as described previously in Scheme A.

The following example presents a typical syntheses as described in Scheme C. This example is understood to be illustrative only and is not intended to limit the scope of the present invention in any way.

EXAMPLE 6

2,6-diethyl-4-[2-(trimethylsilyl)ethyl]-phenol

Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 4-bromomethyl-2,6-diethylphenol (2.43 g, 10 mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

The following compounds can be prepared by procedures analogous to those described above in Examples 5 and 6:

2,6-dipropyl-4-[2-(trimethylsilyl)ethyl]-phenol
2,6-dipropyl-4-[2-(dimethylphenylsilyl)ethyl]-phenol
2,6-diisopropyl-4-[2-(trimethylsilyl)ethyl]-phenol
2,6-diisopropyl-4-[2-(dimethylphenylsilyl)ethyl]-phenol
2,6-diisobutyl-4-[2-(trimethylsilyl)ethyl]-phenol
2,6-diisobutyl-4-[2-(dimethylphenylsilyl)ethyl]-phenol
2,6-dibutyl-4-[2-(trimethylsilyl)ethyl]-phenol
2,6-dibutyl-4-[2-(dimethylphenylsilyl)ethyl]-phenol
2,6-di-t-butyl-4-[2-(trimethylsilyl)ethyl]-phenol
2,6-di-t-butyl-4-[2-(dimethylphenylsilyl)ethyl]-phenol
2,6-di-t-butyl-4-[2-(tri-t-butylsilyl)ethyl]-phenol
2,6-di-t-butyl-4-[2-(di-t-butylphenylsilyl)ethyl]-phenol
2,6-dimethyl-4-[2-(trimethylsilyl)ethyl]-phenol
2,6-dimethyl-4-[2-(dimethylphenylsilyl)ethyl]-phenol.

The present invention also relates to the use of compounds of the formula (1) in inhibiting the peroxidation of LDL lipid and in inhibiting the progression of atherosclerosis in patients in need thereof.

As used herein, the term "patient" refers to warm-blooded animals or mammals, including rodents and humans, who are in need of treatment for atherosclerosis.

Atherosclerosis is a disease state characterized by the development and growth of atherosclerotic lesions or plaque. The identification of those patients who are in need of treatment for atherosclerosis is well within the ability and knowledge of one skilled in the art. For example, individuals who are either suffering from clinically significant atherosclerosis or who are at risk of developing clinically significant atherosclerosis are patients in need of treatment for atherosclerosis. A clinician skilled in the art can readily determine, by the use of clinical tests, physical examination and medical/family history, if an individual is a patient in need of treatment for atherosclerosis.

An effective antiatherosclerotic amount of a compound of formula (1) is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation.

Peroxidation of LDL lipid, such as the unsaturated fatty acid portions of LDL cholesteryl esters and phosholipids, is known to facilitate the deposition of cholesterol in macrophages which subsequently are deposited in the vessel wall and are transformed into foam cells. The identification of those patients who are in need of inhibition of peroxidation of LDL lipid is well within the ability and knowledge of one skilled in the art. For example, those individuals who are in need of treatment for atherosclerosis as defined hereinabove, are also patients who are in need of inhibition of peroxidation of LDL lipid. An effective antioxidant amount of a compound of formula (1) is an amount which is effective in inhibiting the peroxidation of LDL lipid in the patient's blood.

An effective antiatherosclerotic or antioxidant dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antiatherosclerotic or antioxidant amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The following examples illustrate the use of compounds of formula (1) according to the present invention. These examples are illustrative only and are not intended to limit the scope of the invention in any way.

EXAMPLE 7

Inhibition of LDL Lipid Peroxidation

The degree of inhibition of LDL lipid peroxidation was determined by the method of Yagi et al. [*Vitamins* 39, 105 (1968)].

A 0.5 mL solution containing 250 micrograms (µg) of human LDL was incubated with the test compound, in amounts varying from 0 to 30 µg, for 30 minutes at 42° C. To this mixture was added 1 mL of a cupric sulfate solution (final concentration 12.5 µM) and the mixture was incubated at 37° C. for 2.5 hours. The amount of peroxidation of LDL lipid was determined by the thiobarbituric acid assay. The concentration of test compound required to inhibit 50% of LDL lipid peroxidation ($ID_{50}$) was determined.

TABLE 1

| Effect of Test Compounds on LDL Peroxidation | |
|---|---|
| Test Compound[a] | $ID_{50}$ |
| A | 2.8 μM |
| B | 3.0 μM |

[a]Compound A = 2,6-Di-t-butyl-4[(trimethylsilyl)methyl]thio-phenol
Compound B = 2,6-Di-t-butyl-4[(dimethylphenylsilyl)methyl]thio-phenol As with any group of structurally related compounds which possess a particular generic utility, certain groups and configurations are preferred for the compounds of formula (1) in their end use application. With respect to substituents $R_1$ and $R_2$, compounds of formula (1) wherein $R_1$ and $R_2$ are tertiarybutyl are generally preferred. With respect to substituents $R_3$ and $R_4$, compounds of formula (1) wherein $R_3$ and $R_4$ are methyl or ethyl are generally preferred with methyl being especially preferred. With regard to the group Z, compounds of formula (1) wherein Z is thio are preferred. With regard to group A, compounds of formula (1) wherein A is methylene are preferred. Finally, with respect to $R_5$, compounds of formula (1) wherein $R_5$ is methyl, ethyl or substituted or unsubstituted phenethyl are preferred. Compounds of formula (1) wherein $R_5$ is substituted or unsubstituted phenyl are especially preferred.

In addition, the compounds of formula (1) can be used as chemical antioxidant additives in organic materials normally subject to oxidative deterioration, such as, for example, rubber, plastics, fats, petroleum products and the like. In general, a preservative amount of a compound of formula (1), which is sufficient in concentration to inhibit oxidative deterioration of the material to be protected, is admixed with the material subject to oxidation. This preservative amount of a compound of formula (1) will generally vary from about 0.01% to about 1.0% by weight.

What is claimed is:

1. A compound of the formula

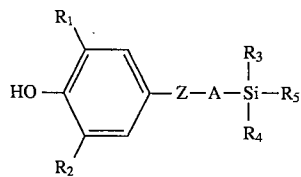

wherein $R_1$, $R_2$, $R_3$ and $R_4$ are each independently a $C_1$–$C_6$ alkyl group;

Z is a methylene group;

A is a $C_1$–$C_4$ alkylene group;

$R_5$ is a $C_1$–$C_6$ alkyl or —$(CH_2)_n$—(Ar)

wherein n is an integer 0 or 1; and Ar is phenyl, or napthyl unsubstituted or substituted with one to three substituents selected from the group consisting of hydroxy, methoxy, ethoxy, chloro, fluoro or $C_1$–$C_6$ alkyl.

2. A compound of claim 1 wherein $R_1$ and $R_2$ are tertiarybutyl.

3. A compound of claim 2 wherein A is methylene.

4. A compound of claim 1 wherein the compound is 2,6-dimethyl-4[2-(trimethylsilyl)ethyl]phenol.

5. A compound of claim 1 wherein the compound is 2,6-diethyl-4-[2-(trimethylsilyl)ethyl]-phenol.

6. A method of inhibiting the progression of atherosclerosis in a patient in need thereof comprising administering to said patient an effective antiatherosclerotic amount of a compound of the formula

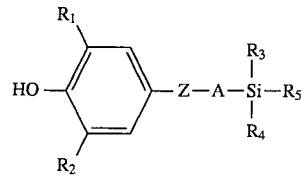

wherein $R_1$, $R_2$, $R_3$ and $R_4$ are each independently a $C_1$–$C_6$ alkyl group;

Z is a thio, oxy or methylene group;

A is a $C_1$–$C_4$ alkylene group;

$R_5$ is a $C_1$–$C_6$ alkyl or —$(CH_2)_n$—(Ar)

wherein n is an integer 0 or 1; and Ar is phenyl, or napthyl unsubstituted or substituted with one to three substituents selected from the group consisting of hydroxy, methoxy, ethoxy, chloro, fluoro or $C_1$–$C_6$ alkyl.

7. A method of inhibiting the peroxidation of LDL lipid in a patient in need thereof comprising administering to said patient an effective antioxidant amount of a compound of the formula

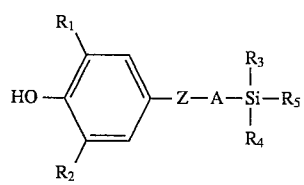

wherein $R_1$, $R_2$, $R_3$ and $R_4$ are each independently a $C_1$–$C_6$ alkyl group;

Z is a thio, oxy or methylene group;

A is a $C_1$–$C_4$ alkylene group;

$R_5$ is a $C_1$–$C_6$ alkyl or —$(CH_2)_n$—(Ar)

wherein n is an integer 0 or 1; and Ar is phenyl, or napthyl unsubstituted or substituted with one to three substituents selected from the group consisting of hydroxy, methoxy, ethoxy, chloro, fluoro or $C_1$–$C_6$ alkyl.

* * * * *